(12) United States Patent
Kostenis et al.

(10) Patent No.: US 7,300,764 B2
(45) Date of Patent: Nov. 27, 2007

(54) METHOD FOR IDENTIFYING AGONISTS AND ANTAGONISTS OF THE GPR45-LIKE/GPR63 RECEPTOR

(75) Inventors: Evi Kostenis, Grebenau (DE); Johann Gassenhuber, Wiesbaden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/455,127

(22) Filed: Jun. 5, 2003

(65) Prior Publication Data

US 2003/0235871 A1 Dec. 25, 2003

Related U.S. Application Data

(60) Provisional application No. 60/408,599, filed on Sep. 6, 2002.

(30) Foreign Application Priority Data

Jun. 8, 2002 (DE) ................ 102 25 651

(51) Int. Cl.
*G01N 33/566* (2006.01)
(52) U.S. Cl. .............. 435/7.21; 435/7.1; 435/7.2; 436/501
(58) Field of Classification Search ............... 435/7.21; 436/501
See application file for complete search history.

(56) References Cited

U.S. PATENT DOCUMENTS

| 5,854,004 | A | 12/1998 | Czernilofsky et al. |
| 6,252,056 | B1 | 6/2001 | Fkushima et al. |
| 6,566,096 | B2 * | 5/2003 | Munroe et al. ............ 435/69.1 |

FOREIGN PATENT DOCUMENTS

| EP | 1 029 916 | | 8/2000 |
| WO | WO99/24569 | * | 5/1999 |
| WO | WO99/67383 | | 12/1999 |
| WO | WO 01/07606 | | 2/2001 |
| WO | WO 01/71022 | | 9/2001 |
| WO | WO 02/34781 | | 5/2002 |

OTHER PUBLICATIONS

An Songzhu et al., Signaling Mechanisms And Molecular Characteristics Of G Protein-Coupled Receptors For Lysophosphatidic Acid And Sphingosine 1-Phosphate, Journal Of Cellular Biochemistry Supplements, (1998), vol. 30/31, pp. 147-157.
Beal Peter A. et al., Second Structural Motif For Recognition Of DNA by Oligonucleotide-Directed Triple-Helix Formation, Science, (1991), vol. 251, pp. 1360-1363.
Cohen Jack S., Oligodeoxynucleotides Antisense Inhibitors Of Gene Expression, Topics in Molecular And Structural Biology, (1989), Catalog No. 7118, ISBN No. 0-8493-7118-X, ISSN No. 0265-4377, Edited By Jack S. Cohen.
Conklun Bruce R. et al., Substitution Of Three Amino Acids Switches Receptor Sepcificity Of Gq Alpha To That Of Gi Alpha, Nature, (1993), vol. 363, pp. 274-276.
Cooney Michael et al., Site-Specific Oligonucleotide Binding Represses Transcription Of The Human c-myc Gene In Vitro, Science, (1998), vol. 241, pp. 456-459.
Iscove N.N. et al., Complete Replacement Of Serum By Albumin, Transferrin, And Soybean Lipid In Cultures Of Lipopolysaccharide-Reactive B Lymphocytes, The Journal Of Experimental Medicine, (1978), vol. 147, pp. 923-933.
Kawasawa Yuka et al., Mammalian PSP24s (Alpha and Beta Isoforms) Are Not Responsive To Lysophosphatidic Acid In Mammalian Expression Systems, Biochemical and Biophysical Research Communications, (2000), vol. 276, pp. 957-964.
Lee Dennis K. et al., Identification Of Four Novel Human G Protein-Coupled Receptors Expressed In The Brain, Molecular Brain Research, (2001), vol. 86, pp. 13-22.
Lee Jeremy S. et al., Complexes Formed By (pyrimidine)n DNAs On Lowering The pH Are Three-Stranded, Nucleic Acids Research, (1979), vol. 6, No. 9, pp. 3073-3091.
Niedernberg Anke et al., Sphingosine 1-Phosphate And Dioleoylphosphatidic Acid Are Low Affinity Agonists For The Orphan Receptor GPR63, Cellular Signalling, (2003), vol. 15, pp. 435-446.
Okano Hideyuki et al., Myelin Basic Protein Gene And The Function Of Antisense RNA In Its Repression In Myelin-Deficient Mutant Mouse, Journal Of Neurochemistry, (1991), pp. 560-563.

* cited by examiner

*Primary Examiner*—John Ulm

(57) ABSTRACT

Embodiments of the present invention relate to methods for identifying compounds which modify the activity of the G protein-coupled receptor GPR45 like/GPR63, compositions useful for this method, and compounds identified by it.

7 Claims, 14 Drawing Sheets

Nucleotide sequence (SEQ ID NO:1) of the GPR45like/GPR63 receptor

```
atggtcttct cggcagtgtt gactgcgttc cataccggga catccaacac aacatttgtc   60
gtgtatgaaa acacctacat gaatattaca ctccctccac cattccagca tcctgacctc  120
agtccattgc ttagatatag ttttgaaacc atggctccca ctggttlgag ttccttgacc  180
gtgaatagta cagctgtgcc cacaacacca gcagcattta agagcctaaa cttgcctctt  240
cagatcaccc tttctgctat aatgatattc attctgtttg tgtcttttct tgggaacttg  300
gttgtttgcc tcatggttta ccaaaaagct gccatgaggt ctgcaattaa catcctcctt  360
gccagcctag cttttgcaga catgttgctt gcagtgctga acatgcccct tgccctggta  420
actattctta ctacccgatg gattttggg aaattcttct gtagggtatc tgctatgttt  480
ttctggttat ttgtgataga aggagtagcc atcctgctca tcattagcat agataggttc  540
cttattatag tccagaggca ggataagcta aacccatata gagctaaggt tctgattgca  600
gtttcttggg caacttcctt ttgtgtagct tttcctttag ccgtaggaaa ccccgacctg  660
cagatacctt cccgagctcc ccagtgtgtg tttgggtaca caaccaatcc aggctaccag  720
gcttatgtga ttttgatttc tctcatttct ttcttcatac ccttcctggt aatactgtac  780
tcatttatgg gcatactcaa caccttcgg cacaatgcct tgaggatcca tagctaccct  840
gaaggtatat gcctcagcca ggccagcaaa ctgggtctca tgagtctgca gagacctttc  900
cagatgagca ttgacatggg ctttaaaaca cgtgccttca ccactatttt gattctcttt  960
gctgtcttca ttgtctgctg ggccccattc accacttaca gccttgtggc aacattcagt 1020
aagcactttt actatcagca caacttttttt gagattagca cctggctact gtggctctgc 1080
tacctcaagt ctgcattgaa tccgctgatc tactactgga ggattaagaa attccatgat 1140
gcttgcctgg acatgatgcc taagtccttc aagtttttgc cgcagctccc tggtcacaca 1200
aagcgacgga tacgtcctag tgctgtctat gtgtgtgggg aacatcggac ggtggtgtga 1260
```

FIG. 1A

Amino acid sequence (SEQ ID NO:2) of the GPR45like/GPR63 receptor

```
Met Val Phe Ser Ala Val Leu Thr Ala Phe His Thr Gly Thr Ser Asn
 1               5                  10                  15

Thr Thr Phe Val Val Tyr Glu Asn Thr Tyr Met Asn Ile Thr Leu Pro
                20                  25                  30

Pro Pro Phe Gln His Pro Asp Leu Ser Pro Leu Leu Arg Tyr Ser Phe
            35                  40                  45

Glu Thr Met Ala Pro Thr Gly Leu Ser Ser Leu Thr Val Asn Ser Thr
        50                  55                  60

Ala Val Pro Thr Thr Pro Ala Ala Phe Lys Ser Leu Asn Leu Pro Leu
 65                  70                  75                  80

Gln Ile Thr Leu Ser Ala Ile Met Ile Phe Ile Leu Phe Val Ser Phe
                85                  90                  95

Leu Gly Asn Leu Val Val Cys Leu Met Val Tyr Gln Lys Ala Ala Met
                100                 105                 110

Arg Ser Ala Ile Asn Ile Leu Leu Ala Ser Leu Ala Phe Ala Asp Met
            115                 120                 125

Leu Leu Ala Val Leu Asn Met Pro Phe Ala Leu Val Thr Ile Leu Thr
            130                 135                 140
```

FIG. 1B

Thr Arg Trp Ile Phe Gly Lys Phe Phe Cys Arg Val Ser Ala Met Phe
145                 150                 155                 160

Phe Trp Leu Phe Val Ile Glu Gly Val Ala Ile Leu Leu Ile Ile Ser
            165                 170                 175

Ile Asp Arg Phe Leu Ile Ile Val Gln Arg Gln Asp Lys Leu Asn Pro
        180                 185                 190

Tyr Arg Ala Lys Val Leu Ile Ala Val Ser Trp Ala Thr Ser Phe Cys
        195                 200                 205

Val Ala Phe Pro Leu Ala Val Gly Asn Pro Asp Leu Gln Ile Pro Ser
    210                 215                 220

Arg Ala Pro Gln Cys Val Phe Gly Tyr Thr Thr Asn Pro Gly Tyr Gln
225                 230                 235                 240

Ala Tyr Val Ile Leu Ile Ser Leu Ile Ser Phe Phe Ile Pro Phe Leu
            245                 250                 255

Val Ile Leu Tyr Ser Phe Met Gly Ile Leu Asn Thr Leu Arg His Asn
            260                 265                 270

Ala Leu Arg Ile His Ser Tyr Pro Glu Gly Ile Cys Leu Ser Gln Ala
        275                 280                 285

Ser Lys Leu Gly Leu Met Ser Leu Gln Arg Pro Phe Gln Met Ser Ile
    290                 295                 300

FIG. 1C (cont'd from FIG. 1B)

```
Asp Met Gly Phe Lys Thr Arg Ala Phe Thr Thr Ile Leu Ile Leu Phe
305                 310                 315                 320

Ala Val Phe Ile Val Cys Trp Ala Pro Phe Thr Thr Tyr Ser Leu Val
                325                 330                 335

Ala Thr Phe Ser Lys His Phe Tyr Tyr Gln His Asn Phe Phe Glu Ile
                340                 345                 350

Ser Thr Trp Leu Leu Trp Leu Cys Tyr Leu Lys Ser Ala Leu Asn Pro
                355                 360                 365

Leu Ile Tyr Tyr Trp Arg Ile Lys Lys Phe His Asp Ala Cys Leu Asp
370                 375                 380

Met Met Pro Lys Ser Phe Lys Phe Leu Pro Gln Leu Pro Gly His Thr
385                 390                 395                 400

Lys Arg Arg Ile Arg Pro Ser Ala Val Tyr Val Cys Gly Glu His Arg
                405                 410                 415

Thr Val Val
```

FIG. 1D (cont'd from FIG. 1C)

SEQ ID NO:3:

5'-CCG CCG AAG CTT GCC ATG GTC TTC TCG GCA GTG TTG ACT GCG-3'

FIG. 2A

SEQ ID NO:4:

5'-GCC GGC GAA TTC TCA CAC CAC CGT CCG ATG TTC CCC-3'

FIG. 2B

SEQ ID NO:5:

5'-CCC ACT GGT TTG AGT TCC TTG ACC-3'

FIG. 3A

SEQ ID NO:6:

5'-GGT AGC CTG GAT TGG TTG TGT ACC-3'

FIG. 3B

SEQ ID NO:7:

5'- CTC AAC ACC CTT CGG CAC-3'

FIG. 4A

SEQ ID NO:8:

5'-GGCC TGG CTG AGG CAT ATAC-3'

FIG. 4B

SEQ ID NO:9:

5'-TGC CTT GAG GAT CCA TAG CTA CCC TGA A-3'

FIG. 4C

SEQ ID NO:10:

5'-TGCC TGG ACA TGA TGC CTA A-3'

FIG. 5A

SEQ ID NO:11:

5'-TCC GTC GCT TTG TGT GAC C-3'

FIG. 5B

SEQ ID NO:12:

5'-TCC TTC AAG TTT TTG CCG CAG CTC C-3'

FIG. 5C

METHOD FOR IDENTIFYING AGONISTS AND ANTAGONISTS OF THE GPR45-LIKE/GPR63 RECEPTOR

This application claims the benefit of priority under 35 U.S.C. § 119 of German Application No. 10225651.9, filed on Jun. 8, 2002, and of U.S. Provisional Application No. 60/408,599, filed on Sep. 6, 2002, the contents of both of which are hereby incorporated by reference.

FIELD OF THE INVENTION

Embodiments of the present invention relate to methods for identifying compounds that modify the activity of the G protein-coupled receptor GPR45 like/GPR63, compositions useful for this method, and compounds identified by it.

BACKGROUND OF THE INVENTION

G protein-coupled receptors mediate extracellular signals from, for example, hormones, neurotransmitters, light and odorants via G proteins into the interior of the cell, and various effects can be initiated via an intracellular signal cascade. G proteins normally consist of three different subunits (alpha, beta, and gamma). Various heterodimeric G proteins which differ in receptor specificity and effect are known. The G proteins are activated by GTP. A well-known G protein is transducin from the vision process.

G protein-coupled receptors (GPCR) play an important part in a large number of physiological processes. They are one of the largest protein families known. It is currently estimated that about 1,000 genes in the human genome code for this class of receptors. GPCR are membrane proteins with 7 transmembrane α-helices. A large number of medicaments displays its effect via GPCRs.

GPCRs are involved especially in signal processing and control of the organism and therefore play a important part in maintaining the function of the intact organism.

The binding of an extracellular ligand leads to a conformational change in the relevant GPCR. The conformational change creates the preconditions for interaction with the respectively associated G protein. The G protein in turn initiates an intracellular signal cascade which is characteristic of the relevant cell type. The so-called second messengers are characteristic of intracellular signal cascades. By these are meant low molecular weight compounds such as, for example, cAMP (cyclic adenosine monophosphate), cGMP (cyclic guanosine monophosphate) or $Ca^{2+}$. The intracellular signaling is controlled by changes in the concentration of the second messengers. The G proteins and their subunits interact for this purpose with proteins such as adenylate cyclase, phospholipase C or ion channels. The change in the concentration of the second messenger in turn brings about an activation or inactivation of other proteins, especially of kinases and phosphatases. The signal finally terminates in a response typical of the particular cell assembly, for example the expression of a protein.

The heterotrimeric G proteins are located on the inside of the plasma membrane. An activated receptor makes contact with the G protein heterotrimer, which then dissociates an α subunit and the βγ complex. Both the activated α subunit and the βγ complex are able to influence intracellular effector proteins. The G protein α subunit family can be divided into various classes. Known examples are the Gαs, Gαi, Gαq and Gα12 classes. GPCRs are classified according to the activated G proteins.

GPCRs of the Gs class mediate, via activation of Gαs, the stimulation of adenylate cyclase and increase the intracellular cAMP concentration. GPCRs of the Gi class bring about, via activation of Gαi, an inhibition of adenylate cyclase and reduce the intracellular cAMP. GPCRs of the Gq class in turn achieve, via activation of Gαq, a stimulation of various PLCβ isoforms and lead, via hydrolysis of membrane-bound phosphatidylinositol 4,5-biphosphate, to diacylglycerol and inositol triphosphate (IP3). IP3 releases $Ca^{2+}$ from intracellular stores. Most GPCRs are able to make contact with only one G protein β subunit family, i.e. they have selectivity for a particular signal transduction pathway.

G proteins with altered receptor specificity and different attachment to a signal transduction pathway can be constructed by joining together components from different G proteins to give hybrid G proteins by the methods of molecular biology and biochemistry.

Hybrid G proteins are fusion constructs which combine within one protein sequences of different Gα subunits. Thus, for example, it is possible by fusing the receptor recognition region of Gαi with the effector activation region of Gαq to produce a Gαq/i hybrid which receives the signals of Gi-coupled receptors but switches on the Gαq PLCβ signal transduction pathway. Such a hybrid in which the C-terminal 5 amino acids of Gαq have been replaced by the corresponding Gαi sequence (Gαiq5) was described for the first time by Conklin et al. Nature 363, 274-276 (1993).

This "rerouting" of receptors has the advantage that the assay endpoint (increase in intracellular $Ca^{2+}$ concentration compared with inhibition of adenylate cyclase) is more easily accessible by measurement techniques and can be used in high throughput screening.

The nucleotide sequence and amino acid sequence of the GPR45 like/GPR63 receptor are known (Genbank: NM_030784; TREMBL:Q9b2i6). The nucleotide sequence of the GPR45 like/GPR63 receptor is set forth in SEQ ID NO:1, and its amino acid sequence in SEQ ID NO:2.

Prior to the inventor's discovery, no one knew which ligands bound to this receptor, making it impossible to identify any agonists or antagonists to the receptor using current laboratory methods. Agonists and antagonists are usually defined organic molecules with a precise structure and a reproducible process of preparation. They are an important research tool: only with the aid of such compounds is it possible to investigate the function of this receptor in various stages of development, in different tissues, including in normal and pathologically altered tissues, and in environments subject to different external influences.

BRIEF DESCRIPTION OF THE FIGURES

FIGS. 1A and 1B-1D show, respectively, a nucleotide sequence (SEQ ID NO:1) encoding an amino acid sequence (SEQ ID NO:2) of the GPR45 like/GPR63 receptor.

FIGS. 2A and 2B show primers (SEQ ID NO:3 and SEQ ID NO:4, respectively) that may be used for performing polymerase chain reaction (PCR) in one embodiment of the invention. The sequence of SEQ ID NO:3 contains a HindIII cleavage site, and the sequence of SEQ ID NO:4 contains an EcoRI cleavage site.

Figure 3A:
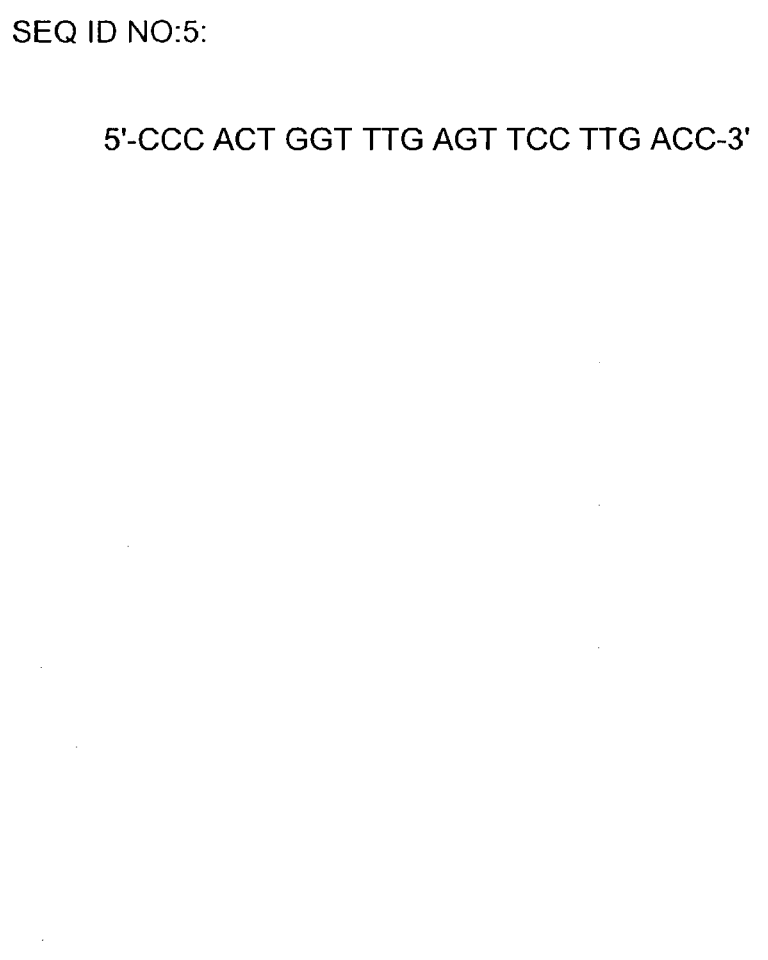

FIGS. 3A and 3B show primers (SEQ ID NO:5 and SEQ ID NO:6, respectively) that may be used for performing another PCR in another embodiment of the invention.

Figure 4A:
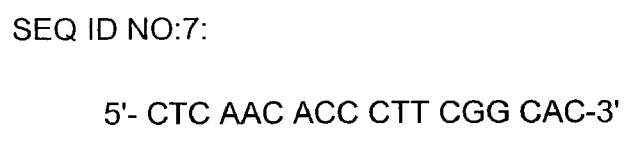

FIGS. 4A-4C show primers (SEQ ID NO:7 and SEQ ID NO:8, respectively) and a TaqMan® probe (SEQ ID NO:9) that may be used in performing PCR in still another embodiment of the invention.

Figure 5A:
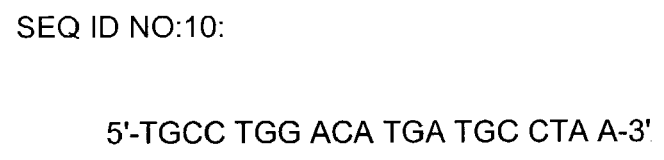
Figure 5B:
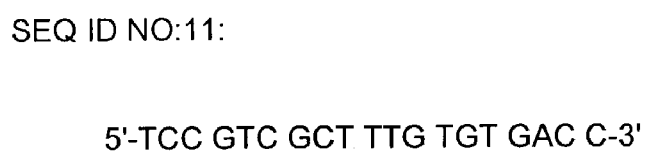

FIGS. 5A-5C show primers (SEQ ID NO:10 and SEQ ID NO:11, respectively) and a TaqMan® probe (SEQ ID NO:12) that may be used in performing PCR in still another embodiment of the invention.

DETAILED DESCRIPTION OF THE INVENTION

The inventors have discovered that Sphingosine 1-phosphate (S1P) and lysophosphatidic acid (LPA) are natural ligands for the GPR45 like/GPR63 receptor. S1P and LPA are lipid signal molecules formed from membrane phospholipids. They are known mainly as intracellular signal molecules. In the case of some GPCRs, S1P or LPA functions as natural ligands. A ligand means a molecule which reversibly binds to a G protein-coupled receptor and exerts via this binding an effect on the receptor (stabilization, inactivation, stimulation). This effect generally relates to a downstream intracellular signal cascade and can be detected from the effects on the signal cascade. A ligand is natural if it is produced by a biological system.

In one embodiment, the invention comprises a method of identifying a compound which modifies the activity of the G protein-coupled receptor, the method comprising:
 a) providing a biological material comprising the receptor and S1P and/or LPA;
 b) providing a chemical compound;
 c) contacting the material of a) with the chemical compound of b); and
 d) determining the activity of the receptor.

The compound can modify the activity of the receptor in several ways, including, for example, by stabilizing it, switching it on, switching it off, or elevating or depressing its signaling.

Bringing the chemical compound into contact with the biological material should preferably take place under conditions which facilitate an interaction between them, such as, for example, under a temperature of about room temperature to about 37° C., and in a pH of about 6 to 8, and more preferably in a pH of about 7.

A G protein-coupled receptor GPR45like/GPR63 is selected from one of the following groups:
 a) a receptor comprising the amino acid sequence as shown in SEQ ID NO:2;
 b) a receptor which is lacking one or more amino acids in relation to the amino acid sequence of SEQ ID NO:2;
 c) a receptor in which one or more amino acids have been added in relation to the amino acid sequence of SEQ ID NO:2; and
 d) a receptor in which one or more amino acids have been replaced by other amino acids in relation to the amino acid sequence of SEQ ID NO:2.

Such receptors will have an amino acid sequence that is at least 80% identical to the amino acid sequence of SEQ ID NO:2 and still retain the function of the G protein-coupled receptor GPR45 like/GPR63. A peptide having a sequence that is at least 97.5% identical to the amino acid sequence of SEQ ID NO:2 is preferred. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code.

The G protein-coupled receptor GPR45 like/GPR63 for carrying out the method described above can be encoded from one of the following groups:
 a) the polynucleotide sequence of SEQ ID NO:1.
 b) a polynucleotide that hybridizes under stringent conditions to the polynucleotide sequence of SEQ ID NO:1;
 c) a polynucleotide that is at least 80% identical over its entire length to the polynucleotide sequence of SEQ ID NO:1;
 d) a polynucleotide that, owing to the degeneracy of the genetic code, encodes a polypeptide encoded by the polynucleotide sequence of SEQ ID NO:1; and
 e) a polynucleotide that, owing to the degeneracy of the genetic code, encodes a polypeptide that is at least 80% identical over its entire length to the polypeptide encoded by the polynucleotide sequence of SEQ ID NO:1.

Hybridization that occurs under "stringent conditions" means that it will occur at 42° C. using, as a hybridization buffer, a solution containing 50% formamide, 5×SSC (0.75 M sodium chloride, 0.075 M sodium citrate), 50 mM sodium phosphate (pH 6.8), 0.1% sodium pyrophosphate, 5× Denhardt reagent, sonicated salmon sperm DNA (50 µg/ml), 0.1% SDS, and 10% dextran sulfate, followed by washing with 0.2×SSC and 0.1% SDS at 42° C. Alternatively, "stringent conditions" means that hybridization will occur at 55° C. using, as a hybridization buffer, a solution containing 50% formamide, 2×SSC, and 10% dextran sulfate, followed by highly stringent washing with 0.1×SSC containing EDTA at 55° C.

The extent to which sequences are "identical" to one another depends on the degree of sequence relatedness between polypeptide or polynucleotide sequences, as the case may be, as determined by the match between strings of such sequences. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman D., SIAM J. Applied Math., 48: 1073 (1988). Preferred methods to determine identity are designed to give the largest match between the sequences tested. Methods to determine identity and similarity are codified in publicly available computer programs. Computer program methods to determine identity and similarity between two sequences include, but are not limited to, the GCG program package (Devereux, J., et al., Nucleic Acids Research 12(1). 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

Any of the variants, described above, from the sequences of SEQ ID NO:1 and SEQ ID NO:2 may be naturally occurring, such as an allelic variant, or may be variants that are not known to occur naturally. Non-naturally occurring variants of polynucleotides and polypeptides may be made by mutagenesis techniques or by direct synthesis.

Preferably, all of the polypeptide variants retain the biological activity of the G protein-coupled receptor GPR45 like/GPR63receptor. Preferred variants are those that vary from the amino acid sequence of SEQ ID NO:2 by conservative amino acid substitutions, that is, those that substitute a residue with another of like characteristics. Typical such substitutions are among Ala, Val, Leu and lie; among Ser and Thr; among the acidic residues Asp and Glu; among Asn and Gln; and among the basic residues Lys and Arg; or aromatic residues Phe and Tyr. Several of the amino acids may be substituted in this manner in any combination.

The G protein-coupled receptor GPR45 like/GPR63 may be in the form of a "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the G protein-coupled receptor GPR45 like/GPR63 may also be used. A fragment is a polypeptide having an amino acid sequence that entirely is the same as part, but not all, of the amino acid sequence of the receptor. Fragments may be "free-standing," or comprised within a larger polypeptide of which they form a part or region, preferably as a single continuous region. Examples of polypeptide fragments include fragments from about amino acid number 1-20, 21-40, 41-60, 61-80, 81-100, and 101 to the end of the amino acid sequence of SEQ ID NO:2. Further examples include truncation polypeptides having the amino acid sequence of SEQ ID NO:2 except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

The G protein-coupled receptor GPR45 like/GPR63 for carrying out the method of the invention can be produced by expression of an exogenous DNA sequence in a prokaryote or eukaryote. Recombinant vector constructions can be produced with the assistance of relevant expert knowledge as described, for example, in CURRENT PROTOCOLS IN MOLECULAR BIOLOGY, F. M. Ausubel et al., eds., Wiley & Sons, New York (2001) (ISBN 0-471-50338-X) or in J. Sambrook, E. F. Fritsch, T. Maniatis, MOLECULAR CLONING, second edition, Cold Spring Harbor Laboratory Press (ISBN 0-87969-309-6). This entails a polynucleotide coding for an amino acid sequence as shown in one of the sequence descriptions (SEQ ID NO:1, and the variants described above) or a polynucleotide sequence as shown in one of the sequence descriptions (SEQ ID NO:2, and its variants described above) being incorporated into a basic vector.

Suitable in principle for producing the protein is any prokaryotic or eukaryotic plasmid vector, bacteriophase vector or yeast plasmid vector. Examples of such vectors are pBR322, pUC18,19, pBluescript, pcDNA3.1 and others. The vector may further comprise a plasmid having an antibiotic resistance marker, an origin of replication suitable for replication of the plasmid in bacteria or cell cultures, and a promoter suitable for expression of a protein. The basic vector may also comprise, for example, a phage vector, a phagemid vector, a phasmid vector, a cosmid vector, a virus vector, a YAC vector or other vector type. Incorporation of the polynucleotide which is to be incorporated takes place via suitable restriction cleavage sites using the appropriate restriction enzymes which are commercially available from companies such as BioLabs, Roche Diagnostics, Stratagene and others. Such restriction cleavage sites may be, for example, the recognition sites of the restriction enzymes BamHI, EcoRI, SalI, EcoRV and others.

The recombinant vector construction comprises in a preferred embodiment an expression vector which can be used in eukaryotes and/or prokaryotes. An expression vector comprises a promoter which can be functionally connected to a polynucleotide sequence so that a protein encoded by this polynucleotide sequence is synthesized in a biological organism, for example a bacterium, fungus or the cell of a eukaryotic cell line. The promoter may be inducible for example by tryptophan or in a constitutive activity.

The S1P and LPA ligands may already be present in the biological material or the preparation of biological material. However, they can also be added from outside. For this purpose, the ligand should be present in an amount, concentration and degree of purity such that its binding to the receptor and initiation of the receptor signal is brought about.

Adding the ligand preferably takes place after the biological material or a preparation of the biological material, each of which contain the G protein-coupled receptor GPR45 like/GPR63, is available in a suitable way (in terms of both composition and amount).

S1P and LPA may comprise a label which can be detected by a suitable detection method. Such a label is, for example, a radioactive label or a fluorometrically detectable label.

Biological material is any material which contains genetic information and can itself reproduce or be reproduced in a biological system. Examples of biological material are cells from human or animal tissues or organs such as, for example, brain, adipose tissue, lung, heart, liver, kidney, spleen, muscle or others. Examples of biological material are also bacteria or fungi such as, for example, *Escherichia coli* or *Saccharomyces cerevisiae*. Biological material also encompasses cells from cell cultures.

Biological material can be obtained in the case of cells from animal or human tissues by biopsy, surgical removal, removal by means of syringes or catheters or comparable techniques. The cells removed in this way can be deep-frozen, worked up or put in cell culture. Bacteria and yeast cells are grown and worked up using conventional techniques of microbiology. The skilled worker will find appropriate instructions for the preservations and use of all these cells in CURRENT PROTOCOLS IN MOLECULAR BIOLOGY, F. M. Ausubel et al., eds., Wiley & Sons, New York (2001) (ISBN 0-471-50338-X).

Biological material may also comprise cells of an animal cell culture. Examples of such cells are mouse cells, rat cells or hamster cells. The cell culture cells may be primary cell types or established cell lines. Examples of established cell lines are mouse 3T3 cells, CHO cells or Hela cells. The maintenance, culturing and growing of cell lines is described in standard textbooks such as, for example, in "Basic Cell Culture; ed.: J. M. Davis IRL Press, Oxford (1996)".

A preparation of a biological material is produced by, for example, disruption of the biological material and subsequent purification steps. Methods for disruption of the biological material include, for example, repeated freezing and thawing, treatment with ultrasound, the use of a French press, addition of detergents and enzymes or similar substances. Subsequent purification steps consist, for example, of differential centrifugation, precipitation with ammonium sulfate or organic solvents, use of chromatographic techniques and others. Chromatographic techniques are, for example, polyacrylamide gel electrophoresis, high pressure liquid chromatography, ion exchange chromatography, affinity chromatography, gas chromatography, mass spectrometry and others. For this, and also for the purification of proteins, detailed instructions are available to the skilled worker in textbooks such as, for example, CURRENT PROTOCOLS IN MOLECULAR BIOLOGY, F. M. Ausubel et al., eds., Wiley & Sons, New York (2001) (ISBN 0-471-50338-X).

The biological material or the preparation of biological material can be brought into contact with a chemical compound in conventional laboratory vessels such as, for example, Eppendorf vessels, centrifuge tubes or glass flasks. The underlying aqueous medium comprises, for example, buffer substances, nutrient constituents, singly charged or doubly charged ions such as $Na^+$, $K^+$, $Ca^{2+}$, $Cl^-$, $SO_4^{2-}$, $PO_3^{2-}$ or others, also proteins, glycerol or others. Particular constant conditions such as, for example, the temperature, the pH, the ionic conditions, the concentration of a protein, the volume or other factors may be advantageous for the bringing into contact. This is achieved by, for example, carrying out the bringing into contact in incubation apparatuses kept at a constant temperature, in the presence of a buffer or with the previously accurately weighed amounts of the ions or proteins. The aqueous solvent may also comprise a certain proportion of an organic solvent such as dimethyl sulfoxide, methanol or ethanol. The content of such a solvent is, however, preferably not more than 10% by volume of the mixture.

The provision of a chemical compound takes place for example by chemical synthesis. The skilled worker is familiar with standard methods of synthesis. The chemical compound may be part of a collection of chemical compounds like those produced by storage and cataloging of the chemical compounds from closed synthesis programs (called chemical libraries). The compound may in other cases have been produced by a microorganism, such as a bacterium, but also by a fungus or a plant (yielding a natural product). Additional examples are provided below.

One can determine the activity of the G protein-coupled receptor GPR45 like/GPR63 according to any of the various methods known in the art to assay receptor activity; the person of ordinary skill the art, having the ligands S1P and LPA at his or her disposal, should have no difficulty selecting the proper method.

One can determine whether a compound is an antagonist to the G protein-coupled receptor GPR45like/GPR63 by, for example, determining the extent to which the compound inhibits S1P and LPA from binding to the receptor. One such method involves transfecting a eucaryotic cell with any of the various polynucleotides described above such that the cell expresses the receptor on its surface. The cell is then contacted with a potential antagonist (that is, the chemical compound) in the presence of a labeled form of S1P or LPA. The ligand can be labeled by, for example, radioactivity; alternatively, it could be a fluorometrically detectable label. The amount of labeled ligand bound to the receptors is measured by, for example, measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

In another screening procedure, one loads a eucaryotic cell, transfected as described above, with an indicator dye that produces a fluorescent signal when bound to calcium. One then adds S1P or LPA and contacts the cells with the chemical compound to be tested. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

One can also transfect a eucaryotic cell with a reporter gene construct in addition to any of the various polynucleotides of the invention. The construct is coupled to activation of the receptor (for example, luciferase or beta-galactosidase behind an appropriate promoter). One then adds S1P or LPA and contacts the cells with the chemical compound to be tested. After a defined period of time, one measures the signal produced. One can use for this purpose a luminometer, spectrophotometer, fluorimeter, or other such instrument appropriate for the specific reporter construct used. Inhibition of the signal generated by the ligand indicates that a compound is a potential antagonist for the receptor.

Another method involves screening for antagonists by determining inhibition or stimulation of G protein-coupled receptor GPR45 like/GPR63-mediated cAMP and/or adenylate cyclase accumulation or dimunition. Such a method involves transiently or stably transfecting a eucaryotic cell with a polynucleotide of the invention. The cell is then exposed to potential antagonists in the presence of S1P or LPA. The amount of cAMP accumulation is then measured, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits receptor binding, the levels of receptor-mediated camp, or adenylate cyclase activity, will be reduced or increased.

Examples of potential receptor antagonists include antibodies or, in some cases, oligonucleotides, which bind to the receptor but do not elicit a second messenger response such that the activity of the receptor is prevented.

Potential antagonists also include an antisense construct prepared through the use of antisense technology. For example, the 5' coding portion of the polynucleotide sequence, which encodes for the mature polypeptides of the present invention, may be used to design an antisense RNA oligonucleotide of from about 10 to 40 base pairs in length. A DNA oligonucleotide is designed to be complementary to a region of the gene involved in transcription (triple helix—see Lee, et al. Nucl. Acids Res., 6: 3073 (1979); Cooney, et al, Science, 241: 456 (1988); and Dervan, et al., Science, 251: 1360 (1991)), thereby preventing transcription and production of the G protein-coupled receptor GPR45 like/GPR63. The antisense RNA oligonucleotide hybridizes to the mRNA in vivo and blocks translation of the mRNA molecule to the receptor. (Okano, J., Neurochem., 56: 560 (1991); OLIGODEOXYNUCLEOTIDES AS ANTISENSE INHIBITORS OF GENE EXPRESSION, CRC Press, Boca Raton, Fla. (1988)). The oligonucleotides described above can also be delivered to cells such that the antisense RNA or DNA may be expressed in vivo to inhibit production of the receptor.

Another potential antagonist is a small molecule which binds to the G protein-coupled receptor GPR45 like/GPR63, making it inaccessible to ligands such that normal biological activity is prevented. Examples of small molecules include, but are not limited to, small peptides or peptide-like molecules.

Potential antagonists also include soluble forms of the G protein-coupled receptor GPR45 like/GPR63, such as fragments of the polypeptide, which bind to the ligand and prevent the ligand from interacting with membrane bound Human GPR14 polypeptides.

Human G protein-coupled receptor GPR45 like/GPR63 are believed to be responsible for many biological functions, including many pathologies. Accordingly, it is desirable to find compounds and drugs which stimulate the receptor, on the one hand, and which can inhibit its function on the other. In general, agonists are employed for therapeutic and prophylactic purposes for such conditions as ischemic coronary artery disease (angina and myocardial infarction), atherosclerosis, metabolic diseases (e.g., diabetes), CHF/myocardial dysfunction, arrhythmias, restenosis, hypertension, hypotension, pulmonary disease (hypertension, COPD, asthma), fibrotic vasculopathies (diabetes, SLE, AS, Reynaud's), cerebrovascular events (e.g. hemorrhagic and ischemic stroke), neurogenic inflammation/migraine, hematopoietic disorders, ARDS, cancer, autoimmune diseases (e.g. HIV-1 and -2 infection and AIDS), gastrointestinal and genitourinary disturbances (e.g. ulcers), endocrine disorders, fibroproliferative disorders (e.g. psoriasis), inflammatory disease (e.g. RA, Crohn's, IBS), benign prostatic hypertrophy, renal failure and glomerulopathies, disease states, both cardiovascular and non-cardiovascular, which are characterized by excessive vasoconstriction, myocardial dysfunction and/or aberrant fibroproliferative/inflammatory responses, psychotic and neurological disorders, including anxiety, schizophrenia, manic depression, delirium, dementia, severe mental retardation, Parkinson's disease, and dyskinesias, infections such as bacterial, fungal, protozoan and viral infections, pain, eating disorders, such as obesity, anorexia, and bulimia, asthma, urinary retention, osteoporosis, allergies, Huntington's disease or Gilles de la Tourett's syndrome. Antagonists may be employed for a variety of therapeutic and prophylactic purposes for such conditions as ischemic coronary artery disease (angina and myocardial infarction), atherosclerosis, metabolic diseases (e.g. diabetes), CHF/myocardial dysfunction, arrythmias, restenosis, hypertension, hypotension, pulmonary disease (hypertension, COPD, asthma), fibrotic vasculopathies (diabetes, SLE, AS, Reynaud's), cerebrovascular events (e.g. hemorrhagic and ischemic stroke), neurogenic inflammation/migraine, hematopoietic disorders, ARDS, cancer, autoimmune diseases (e.g. HIV-1 and -2 infection and AIDS), gastrointestinal and genitourinary disturbances (e.g. ulcers), endocrine disorders, fibroproliferative disorders (e.g. psoriasis), inflammatory disease (e.g. RA, Crohn's, IBS), benign prostatic hypertrophy, renal failure and glomerulopathies; disease states, both cardiovascular and non-cardiovascular, which are characterized by excessive vasoconstriction, myocardial dysfunction and/or aberrant fibroproliferative/inflammatory responses; psychotic and neurological disorders, including anxiety, schizophrenia, manic depression, delirium, dementia, severe mental retardation, Parkinson's disease, and dyskinesias; infections such as bacterial, fungal, protozoan and viral infections; pain; eating disorders, such as obesity, anorexia, and bulimia; asthma; urinary retention; osteoporosis; allergies; Huntington's disease or Gilles dela Tourctt's syndrome.

The invention hence further relates to a compound which modifies the activity of the G protein-coupled receptor GPR45 like/GPR63, where the compound has been identified by a method as described above. Such a compound has a mass of preferably between about 0.1 to about 50 kDa, and more preferably between about 0.1 to 5 kDa, and especially preferably between about 0.1 and 3 kDa. The compound may be a protein, an amino acid, a polysaccharide, a sugar, a polynucleotide, a nucleotide, a fatty acid-containing compound, a fat, a fatty acid, a fatty acid derivative or an aromatic hydrocarbon compound. The compound may contain excipients for a medicament and/or other additives. Any such medicament is particularly suitable for the treatment of cardiovascular disorders, such as, but not limited to, the cardiovascular disorders described above.

Suitable pharmaceutical compounds can be administered as medicaments in oral, peroral, topical, parenteral or rectal form. The mode of administration which is most suitable depends in each individual case on the nature and severity of the condition to be treated and on the type of compound used in each case. A suitable active ingredient concentration is about 1% to 35%, and preferably about 3% to 15%.

The invention further relates to the use of a compound which has been identified by a method of the invention for producing a complex of the receptor GPR45 like/GPR63 with this compound. Suitable compounds for producing such a complex are, for example, sphingosine 1-phosphate or lysophosphatidic acid. The invention also relates to a complex of the receptor GPR45 like/GPR63 and sphingosine 1-phosphate and/or lysophosphatidic acid. A complex means in this connection a compound composed of one or more proteins of the receptor in an at least specific binding with sphingosine 1-phosphate and/or lysophosphatidic acid and further lipids, membrane constituents or detergents which are possibly necessary to stabilize the receptor or receptor/ligand complex. The binding is specific if the binding constant is less than or equal to 100 µM.

EXAMPLES

Cloning of the Human GPR45 Like/GPR63 Receptor

The sequence of the human GPR45 like receptor is accessible to the public under numbers AF 31765 and AB 030566 at Genbank and EMBL. The human gene contains no introns. The receptor has therefore been amplified starting from human genomic DNA using a polymerase chain reaction (PCR).

The PCR reaction conditions were as follows: initially incubation at 94° C. for 10 min, then 35 cycles of incubation at 94° C. in each case for 1 min per cycle, then incubation at 60° C. for 1 min and finally incubation at 72° C. for 2 min. The reaction was in this case carried out using the GC-melt Kit from BD Biosciences Clontech, Heidelberg. The primers used as shown in SEQ ID NO:3 and 4 were designed so that they contained a HindIII cleavage site (SEQ ID NO:3) and an EcoRI cleavage site (SEQ ID NO:4):

```
5'-CCG CCG AAG CTT GCC ATG GTC TTC TCG GCA GTG TTG ACT GCG-3'    (SEQ ID NO:3)

5'-GCC GGC GAA TTC TCA CAC CAC CGT CCG ATG TTC CCC-3'            (SEQ ID NO:4)
```

The PCR fragment with a length of 1,260 base pairs which was formed by the PCR described above was incorporated with the aid of the HindIII and EcoRI cleavage sites into the eukaryotic expression vector pCDNA 3.1(+). This vector is commercially obtainable from, for example, Invitrogen Life Technologies, Karlsruhe.

In an Extraction of RNA PCR Using Reverse Transcriptase (RT-PCR)

RNA was isolated from the following cell lines: HUVECS (human umbilical vein endothelial cells), HPAEC (human pulmonary artery endothelial cells), Hek 293 (human embryonic kidney cells), HCASMC (human coronary artery smooth muscle cells), HCAEC (human coronary artery endothelial cells), HMVEC-L (human microvascular endothelial cells of the lung), HPASMC (human pulmonary artery smooth muscle cells), and HAOSMC (human aortic smooth muscle cells).

RNA was isolated from various cell lines using TRIzol reagent from Gibco BRL.

The cells were harvested shortly before confluence was reached in a tissue culture bottle. RNA was isolated from the cells using TRIzol reagent, obtained from the Gibco BRL division of Life Technologies, Inc. of Gaithersburg, Ma., in accordance with the manufacturer's instructions. The RNA was tested for the absence of genomic DNA. About 5 µg of this RNA was used to carry out a reverse transcriptase reaction using MMLV (Moloney murine leukemia virus) reverse transcriptase and the RT-PCR kit from Stratagene. The RT-PCR was carried out in a volume of 50 µl, the reaction being carried out by incubation initially at 65° C. for 5 min, then at room temperature for 15 min, then at 37° C. for 1 hour and then at 90° C. for 5 min and finally by cooling in ice.

The cDNA preparations from these reverse transcriptions were used for the subsequent PCR reactions. Where available, cDNA obtainable commercially was employed.

About 5 µg of cDNA were used for a PCR. The reaction itself is carried out with an Amplitaq Gold Polymerase Kit from Perkin Elmer. The reaction conditions for the cycles are as follows: incubation at 95° C. for 12 min, then 35 cycles incubating at 94° C. in each case initially for 1 min and then incubating at 72° C. for 1 min for each cycle and then, after completing the 35 cycles, incubating at 72° C. for 10 min and finally cooling on ice.

The primers used for this purpose were the two following DNA sequences:

```
                                    (SEQ ID NO:5; "forward")
    5'-CCC ACT GGT TTG AGT TCC TTG ACC-3'

(SEQ ID NO:6; "reverse")
    5'-GGT AGC CTG GAT TGG TTG TGT ACC-3'
```

A product 561 base-pairs long resulted.

Quantitative RT-PCR in Real Time Using TaqMan®

The quantitative PCR analysis was carried out by means of fluorescence resonance energy transfer (FRET). The skilled worker is familiar with this system also under the name TaqMan® PCR. A kit commercially available from Perkin Elmer Life Sciences was used to carry out the TaqMan® reaction. The TaqMan® sample comprises a single-stranded oligonucleotide which is labeled with 2 different fluorophores. The fluorophore at the 3' end (acceptor) acts as "quencher" (i.e. with attenuating effect) of the fluorophore at the 5' end (donor). The Taq DNA polymerase liberates the fluorophore at the 5' end through its 5'-exonuclease activity during the chain-extension reaction. Since the emission of the fluorophore is now no longer quenched, it can be measured by a fluorimeter. The amount of fluorescence found is directly proportional to the amount of the PCR product which accumulates during the amplification. Care should be taken that the melting temperature of the TaqMan® oligo is higher than that of the primer for the amplification by Taq polymerase.

The fluorophores used in the present case were FAM (6-carboxyfluorescein) as donor for the 5' end and TAMRA (5-carboxytetramethylrhodamine) as acceptor/quencher for the 3' end.

The cDNA was produced by using commercially available RNA, for example from BD Biosciences Clontech, Heidelberg.

5 µg of total RNA were mixed with 2.5 µl (5 mg/µl) of hexamer primers of random sequence. Such hexamer primers are available from various companies. In the present case, they were from Invitrogen Life Technologies, Karlsruhe. Total RNA and hexamer primers were first heated at 70° C. for 10 min and cooled on ice. Then 4 µl of 5× buffer (first stand buffer), 2 µl of 0.1 nM DTT (dithiothreitol), 1 µl of 10 mM dNTP and 1 µl of water were-added and, after careful mixing, incubated at 37° C. for 2 minutes. 5 µl of reverse transcriptase were then added, and the mixture was incubated at 37° C. for 60 min. The reaction was stopped by adding 1 µl of 2.5 mM EDTA and heating at 65° C. for 10 min.

The cDNA samples produced in this way served as templates for the subsequent quantitative PCR.

In each case 50 ng/µl, 25 ng/µl, 10 ng/µl, 5 ng/µl, 2.5 ng/µl, 1.25 ng/µl and 0.625 ng/µl final concentration of each reverse-transcribed cDNA template were investigated.

The reaction took place in a total volume of 50 µl. The reaction mixture contains dNTP and buffer in the usual concentrations, and Taq polymerase. The final concentration of the primers was 900 mM in each case.

Comparison with Primers for the Human Beta Aktin Gene in Human Brain cDNA

The determinations were each carried out in duplicate in different batches. The standard values for the human aktin gene were used as internal controls to standardize the samples in the determination of the GPR45 like/GPR63 gene expression to be found in the various RNAs. The expression was expressed as a ratio to a previously defined reference tissue. The reference defined in each case was the cerebellum for the central nervous system and the brain for the peripheral tissue.

The primers used for the amplification reaction in the first determination had the following nucleotide sequence:

```
5'-CTC AAC ACC CTT CGG CAC-3'      (SEQ ID NO:7)
5'-GGCC TGG CTG AGG CAT ATAC-3'.   (SEQ ID NO:8)
```

The TaqMan® oligo sample for this had the nucleotide sequence:

```
5'-TGC CTT GAG GAT CCA TAG CTA CCC TGA
   A-3' (SEQ ID NO:9).
```

The amplification primers in the second determination had the following nucleotide sequence:

```
5'-TGCC TGG ACA TGA TGC CTA A-3'   (SEQ ID NO:10)
5'-TCC GTC GCT TTG TGT GAC C-3'.   (SEQ ID NO:11)
```

The corresponding TaqMan® sample for this had the nucleotide sequence:

```
5'-TCC TTC AAG TTT TTG CCG CAG CTC C-3'
   (SEQ ID NO:12).
```

Northern Blotting

Northern blots with RNA from various human tissues were purchased from BD Biosciences Clontech, Palo Alto. Such Northern blots can also be obtained in the same quality from other suppliers. The nucleotide sequence of the GPR45 like/GPR63 receptor was cut out using EcoRI and HindIII and expression plasma drive from pcDNA 3.1 and was fractionated on an agarose gel and the sequence 1,260 base pairs long was isolated and then radiolabeled with $^{32}$P-dCTP. The Northern blots with the RNA from various tissues were hybridized under stringent conditions. The radioactivity was detected using a film. For internal comparison, the same Northern blots were washed until none of the previously hybridized DNA molecules with the coding sequence for the GPR45 like/GPR63 receptor were detectable any longer. These washed Northern blots were again hybridized using a beta-actin cDNA sample.

Detection of GPR45 Like/GPR63 Receptor Activity in Transfected Cell Cultures

CHO-K1 cells were cultivated in basal Iscove's medium with further additions. Iscove's medium is commercially available from, for example, Biochrom, Berlin. The composition was described for the first time in N. N. Iscove and F. Melchers, *Journal of Experimental Medicine* 147, 923-933 (1978). 10% fetal bovine serum, 10 000 U/ml-10 000 µg/ml penicillin-streptomycin, gentamycin, and 2 mM L-glutamine were used as further additions to Iscove's medium. The cells were incubated at 37° C. with a 5% $CO_2$ atmosphere.

About $2\times10^5$ CHO-K1 cells were seeded in 35 mm dishes for the transient transfection. After further incubation for about 24 hours and with the cells at about 50-80% confluence, the cells were transiently transfected with 1 µg of the plasmid DNA construct with the assistance of Lipofectamine (Gibco).

FLIPR Assay (Fluorometric Imaging Plate Reader Assay)

About 16 to 18 hours after the transfection, the CHO cells were put in an amount of about 80,000 cells per well in 96-well plates and incubated further for about 18-24 hours. 95 µl of HBSS (Hank's buffered saline solution) with 20 mM HEPES, 2.5 mM probenecid (4-[(dipropylamino)sulfonyl] benzoic acid) and 4 µM dye Fluo4 were added to the cells.

The cells were incubated in 5% $CO_2$ for 1 hour and washed three times with PBS (phosphate buffered saline) which contained 1 mM $MgCl_2$, 1 mM EDTA, 0.4 mg/ml FAF-BSA (fatty acid free bovine serum albumin) and 2.5 mM probenecid.

After the last washing step, 100 µl were left on the cells in each well. The lipids to be tested were available as 2 mM stock solution in DMSO (dimethylsulfoxide). A 60 µM solution was kept ready on a 96-well microtiter plate. The stock solution was diluted in PBS. 50 µl portions of this 60 mM solution were transferred into each well of the microtiter plate containing 100 µl of PBS and the cells. A 20 µM final concentration of the lipids to be tested was obtained in this way.

The fluorescence was measured by a Fluorometric Imaging Plate Reader (FLIPR®, Molecular Devices, Sunnyvale, Calif.) for 1 min in intervals lasting 1 sec and for a further 2 min in 3-second intervals.

Cell Growth Assay

CHO cells were put in an amount of $8\times10^4$ cells into 35 mm plates. After 32 hours, the cells were transfected with 1 µg of the plasmid construct using Lipofectamine (Gibco). After a further 13 hours (time 0), the cells were washed with PBS and incubated in Iscove's medium which contained 10% dialyzed fetal calf serum for 48 hours (time 48), specifically in the presence or absence of 1 µM S1P (sphingosine 1-phosphate).

The number of cells at time 0 and time 48 was determined by counting. This was done by first treating the cells with trypsin and then suspending them in 1 ml of Iscove's. An amount of 100 µl of these cells was diluted in 10 ml of buffer and counted in a cell counter, e.g. in the Casy Cellcounter TT (Cell Counter und Analysesystem, Schärfe, Reutlingen).

Specificity of Expression of the GPR45 Like/GPR63 Receptor in Various Human Tissues The expression was investigated using the RT-PCR. Specific transcripts of the GPR45 like/GPR63 receptor were detectable in the aorta, heart, left ventricle, fetal hearts, brain and kidney. Only a weak band was obtainable in tissues from the left atrium. No signal was detectable in lung tissue.

Expression of the GPR45 like/GPR63 Receptor in Various Human Cell Lines

HUVECS (human umbilical vein endothelial cells), HCAEC (human coronary artery endothelial cells), MHVEC-L (human microvascular endothelial cells from lung), HPAEC (human coronary artery smooth muscle cells), HPASMC (human pulmonary artery smooth muscle cells), HAOSMC (human aortic smooth muscle cells) were investigated according to the method described above. Transcripts of the GPR45 like/GPR63 receptor were detectable in all cell lines.

GPR45 like/GPR63 Receptor Expression in Peripheral Human Tissue

Expression of the receptor was determined using the TaqMan® RT-PCR analysis semiquantitatively in relation to the expression in the brain.

An internal comparison took place in relation to the β-actin RNA. Each measurement was determined twice. The following table shows the RNA expression as a multiple of the expression in the brain.

TABLE 1

Expression of the GPR45like/GPR63 receptor in various tissues in relation to the brain

| ORGAN | EXPRESSION RELATIVE TO BRAIN |
|---|---|
| Brain | 1 |
| Heart | 0.1 |
| Kidney | 0.2 |
| Liver | 0.01 |
| Lung | 0.05 |
| Spleen | 0.2 |
| Thymus | 0.6 |
| Skeletal muscle | 0.05 |
| Pancreas | 0.15 |
| Small intestine | 0.8 |
| Stomach | 0.7 |

Relatively strong expression was found in thymus, small intestine and stomach, while almost no expression was detectable in liver, kidney and skeletal muscle.

GPR45 like/GPR63 Receptor Expression in Various Parts of the Brain.

Expression of the receptor was determined using the TaqMan® RT-PCR semiquantitatively in relation to expression in the cerebellum. The internal comparison was in relation to the β-actin RNA. Each measurement was determined twice. The following table shows the expression relative to the cerebellum.

TABLE 2

Expression of the GPR45like/GPR63 receptor in various parts of the brain in relation to the cerebellum

| ORGAN | EXPRESSION RELATIVE TO BRAIN |
|---|---|
| Cerebellum | 1 |
| Whole brain | 1.2 |
| Corpus callosum | 0.2 |
| Caudatus | 1.5 |
| Thalamus | 2.1 |
| Amygdala | 1.2 |

The strongest expression by comparison is observed in the thalamus.

Stimulation of Intracellular $Ca^{2+}$ Release by the GPR45 Like/GPR63 Receptor 209 different bioactive lipids from a substance library were added, each in a final concentration of 1 μM, to CHO cells which expressed the GPR45 like/GPR63 receptor and the G Protein α subunit delta 6qi4mgr (=i49i4). About 30 compounds were tested. Only S1P (sphingosine 1-phosphate) and DHS1P (dihydrosphingosine 1-phosphate) led to a measurable $Ca^{2+}$ influx. The α subunit delta 6qi4mgr (=i4qi4) has a broad specificity in relation to different GPCRs.

Induction of Cell Growth by GPR45 Like/GPR63 Receptors.

An amount of $8 \times 10^4$ CHO cells was seeded onto 35 mm plates. The cells were transfected after 32 hours with 1 μg of DNA of the vector construction. After 13 hours, the cells were washed once with PBS and incubated in Iscove's medium containing 10% dialyzed fetal calf serum in the presence or absence of 1 μM S1P for a further 48 hours. It was possible to show that test mixtures which contained S1P contained about 20% more cells in the average of 2 tests done independently of one another.

What is claimed is:

1. A method for identifying a compound which modifies activity of a G protein-coupled receptor comprising SEQ ID NO:2, the method comprising:
   a) providing a biological material comprising the receptor and a ligand selected from the group consisting of sphingosine 1-phosphate and dihydrosphingosine-1-phosphate;
   b) providing a chemical compound;
   c) contacting the biological material of a) with the chemical compound of b); and
   d) determining the activity of the receptor.

2. The method of claim 1, wherein the receptor is produced by prokaryotic or eukaryotic expression of a DNA encoding the receptor.

3. The method of claim 1, wherein the step of providing a biological material further comprises providing the receptor in a first step and adding the ligand to it in a second step.

4. The method of claim 1, wherein the ligand further comprises a label.

5. The method of claim 1, wherein the ligand further comprises a label.

6. A method for identifying a compound which modifies the activity of a G protein-coupled receptor comprising SEQ ID NO:2, the method comprising:
   a) providing a biological material comprising the receptor and sphingosine 1-phosphate;
   b) providing a chemical compound;
   c) contacting the biological material of a) with the chemical compound of b); and
   d) determining the activity of the receptor.

7. A method for identifying a compound which modifies the activity of a G protein-coupled receptor comprising SEQ ID NO:2, the method comprising:
   a) providing a biological material comprising the receptor and dihydrosphingosine-1-phosphate;
   b) providing a chemical compound;
   c) contacting the biological material of a) with the chemical compound of b); and
   d) determining the activity of the receptor.

* * * * *

SEQUENCE LISTING

<160> NUMBER OF SEQ ID NOS: 12

<210> SEQ ID NO 1
<211> LENGTH: 1260
<212> TYPE: DNA
<213> ORGANISM: Homo sapiens

<400> SEQUENCE: 1

```
atggtcttct cggcagtgtt gactgcgttc cataccggga catccaacac aacatttgtc      60
gtgtatgaaa acacctacat gaatattaca ctccctccac cattccagca tcctgacctc     120
agtccattgc ttagatatag ttttgaaacc atggctccca ctggtttgag ttccttgacc     180
gtgaatagta cagctgtgcc cacaacacca gcagcattta agagcctaaa cttgcctctt     240
cagatcaccc tttctgctat aatgatattc attctgtttg tgtcttttct tgggaacttg     300
gttgtttgcc tcatggttta ccaaaaagct gccatgaggt ctgcaattaa catcctcctt     360
gccagcctag cttttgcaga catgttgctt gcagtgctga acatgccctt tgccctggta     420
```

-continued

```
actattctta ctacccgatg gattttggg aaattcttct gtagggtatc tgctatgttt    480
ttctggttat ttgtgataga aggagtagcc atcctgctca tcattagcat agataggttc    540
cttattatag tccagaggca ggataagcta aacccatata gagctaaggt tctgattgca    600
gtttcttggg caacttcctt ttgtgtagct tttcctttag ccgtaggaaa ccccgacctg    660
cagatacctt cccgagctcc ccagtgtgtg tttgggtaca caaccaatcc aggctaccag    720
gcttatgtga ttttgatttc tctcatttct ttcttcatac ccttcctggt aatactgtac    780
tcatttatgg gcatactcaa caccttcgg cacaatgcct tgaggatcca tagctaccct    840
gaaggtatat gcctcagcca ggccagcaaa ctgggtctca tgagtctgca gagacctttc    900
cagatgagca ttgacatggg ctttaaaaca cgtgccttca ccactatttt gattctcttt    960
gctgtcttca ttgtctgctg ggccccattc accacttaca gccttgtggc aacattcagt   1020
aagcactttt actatcagca caactttttt gagattagca cctggctact gtggctctgc   1080
tacctcaagt ctgcattgaa tccgctgatc tactactgga ggattaagaa attccatgat   1140
gcttgcctgg acatgatgcc taagtccttc aagtttttgc cgcagctccc tggtcacaca   1200
aagcgacgga tacgtcctag tgctgtctat gtgtgtgggg aacatcggac ggtggtgtga   1260
```

<210> SEQ ID NO 2
<211> LENGTH: 419
<212> TYPE: PRT
<213> ORGANISM: Homo sapiens

<400> SEQUENCE: 2

```
Met Val Phe Ser Ala Val Leu Thr Ala Phe His Thr Gly Thr Ser Asn
1               5                   10                  15

Thr Thr Phe Val Val Tyr Glu Asn Thr Tyr Met Asn Ile Thr Leu Pro
            20                  25                  30

Pro Pro Phe Gln His Pro Asp Leu Ser Pro Leu Leu Arg Tyr Ser Phe
        35                  40                  45

Glu Thr Met Ala Pro Thr Gly Leu Ser Ser Leu Thr Val Asn Ser Thr
    50                  55                  60

Ala Val Pro Thr Thr Pro Ala Ala Phe Lys Ser Leu Asn Leu Pro Leu
65                  70                  75                  80

Gln Ile Thr Leu Ser Ala Ile Met Ile Phe Ile Leu Phe Val Ser Phe
                85                  90                  95

Leu Gly Asn Leu Val Val Cys Leu Met Val Tyr Gln Lys Ala Ala Met
                100                 105                 110

Arg Ser Ala Ile Asn Ile Leu Leu Ala Ser Leu Ala Phe Ala Asp Met
            115                 120                 125

Leu Leu Ala Val Leu Asn Met Pro Phe Ala Leu Val Thr Ile Leu Thr
        130                 135                 140

Thr Arg Trp Ile Phe Gly Lys Phe Phe Cys Arg Val Ser Ala Met Phe
145                 150                 155                 160

Phe Trp Leu Phe Val Ile Glu Gly Val Ala Ile Leu Leu Ile Ile Ser
                165                 170                 175

Ile Asp Arg Phe Leu Ile Ile Val Gln Arg Gln Asp Lys Leu Asn Pro
            180                 185                 190

Tyr Arg Ala Lys Val Leu Ile Ala Val Ser Trp Ala Thr Ser Phe Cys
        195                 200                 205

Val Ala Phe Pro Leu Ala Val Gly Asn Pro Asp Leu Gln Ile Pro Ser
    210                 215                 220

Arg Ala Pro Gln Cys Val Phe Gly Tyr Thr Thr Asn Pro Gly Tyr Gln
```

```
                225                 230                 235                 240
Ala Tyr Val Ile Leu Ile Ser Leu Ile Ser Phe Phe Ile Pro Phe Leu
                    245                 250                 255
Val Ile Leu Tyr Ser Phe Met Gly Ile Leu Asn Thr Leu Arg His Asn
                260                 265                 270
Ala Leu Arg Ile His Ser Tyr Pro Glu Gly Ile Cys Leu Ser Gln Ala
            275                 280                 285
Ser Lys Leu Gly Leu Met Ser Leu Gln Arg Pro Phe Gln Met Ser Ile
        290                 295                 300
Asp Met Gly Phe Lys Thr Arg Ala Phe Thr Thr Ile Leu Ile Leu Phe
305                 310                 315                 320
Ala Val Phe Ile Val Cys Trp Ala Pro Phe Thr Thr Tyr Ser Leu Val
                325                 330                 335
Ala Thr Phe Ser Lys His Phe Tyr Tyr Gln His Asn Phe Phe Glu Ile
                340                 345                 350
Ser Thr Trp Leu Leu Trp Leu Cys Tyr Leu Lys Ser Ala Leu Asn Pro
                355                 360                 365
Leu Ile Tyr Tyr Trp Arg Ile Lys Lys Phe His Asp Ala Cys Leu Asp
            370                 375                 380
Met Met Pro Lys Ser Phe Lys Phe Leu Pro Gln Leu Pro Gly His Thr
385                 390                 395                 400
Lys Arg Arg Ile Arg Pro Ser Ala Val Tyr Val Cys Gly Glu His Arg
                    405                 410                 415
Thr Val Val

<210> SEQ ID NO 3
<211> LENGTH: 42
<212> TYPE: DNA
<213> ORGANISM: Homo sapiens

<400> SEQUENCE: 3
ccgccgaagc ttgccatggt cttctcggca gtgttgactg cg                 42

<210> SEQ ID NO 4
<211> LENGTH: 36
<212> TYPE: DNA
<213> ORGANISM: Homo sapiens

<400> SEQUENCE: 4
gccggcgaat tctcacacca ccgtccgatg ttcccc                        36

<210> SEQ ID NO 5
<211> LENGTH: 24
<212> TYPE: DNA
<213> ORGANISM: Homo sapiens

<400> SEQUENCE: 5
cccactggtt tgagttcctt gacc                                     24

<210> SEQ ID NO 6
<211> LENGTH: 24
<212> TYPE: DNA
<213> ORGANISM: Homo sapiens

<400> SEQUENCE: 6
ggtagcctgg attggttgtg tacc                                     24

<210> SEQ ID NO 7
```

```
<211> LENGTH: 18
<212> TYPE: DNA
<213> ORGANISM: Homo sapiens

<400> SEQUENCE: 7
ctcaacaccc ttcggcac                                                  18

<210> SEQ ID NO 8
<211> LENGTH: 20
<212> TYPE: DNA
<213> ORGANISM: Homo sapiens

<400> SEQUENCE: 8
ggcctggctg aggcatatac                                                20

<210> SEQ ID NO 9
<211> LENGTH: 28
<212> TYPE: DNA
<213> ORGANISM: Homo sapiens

<400> SEQUENCE: 9
tgccttgagg atccatagct accctgaa                                       28

<210> SEQ ID NO 10
<211> LENGTH: 20
<212> TYPE: DNA
<213> ORGANISM: Homo sapiens

<400> SEQUENCE: 10
tgcctggaca tgatgcctaa                                                20

<210> SEQ ID NO 11
<211> LENGTH: 19
<212> TYPE: DNA
<213> ORGANISM: Homo sapiens

<400> SEQUENCE: 11
tccgtcgctt tgtgtgacc                                                 19

<210> SEQ ID NO 12
<211> LENGTH: 25
<212> TYPE: DNA
<213> ORGANISM: Homo sapiens

<400> SEQUENCE: 12
tccttcaagt ttttgccgca gctcc                                          25
```